United States Patent [19]

Bradcovich

[11] Patent Number: 4,912,787
[45] Date of Patent: Apr. 3, 1990

[54] HYDRAULIC STRETCHER DEVICE

[75] Inventor: James M. Bradcovich, Akron, Ohio

[73] Assignee: Beta Medical Products, Akron, Ohio

[21] Appl. No.: 132,927

[22] Filed: Dec. 15, 1987

Related U.S. Application Data

[63] Continuation-in-part of Ser. No. 31,652, Mar. 3, 1987, abandoned.

[51] Int. Cl.⁴ ............................................... A61G 1/02
[52] U.S. Cl. ............................................... 5/62; 5/63; 296/20
[58] Field of Search ............................ 5/11, 60, 62–65, 5/427, 430, 503, 508; 378/20, 208, 209; 254/93 R; 296/20

[56] References Cited

U.S. PATENT DOCUMENTS

| | | | |
|---|---|---|---|
| 1,704,979 | 3/1929 | Kusterle et al. | 5/508 |
| 2,014,244 | 9/1935 | Bramlett | 5/11 X |
| 2,387,940 | 10/1945 | Page | 259/93 R X |
| 2,621,574 | 12/1952 | Thomas | 254/93 R |
| 3,253,284 | 5/1966 | St. John | 5/62 |
| 3,393,004 | 6/1968 | Williams | 5/62 X |
| 3,813,712 | 6/1974 | Bonnin . | |
| 3,820,838 | 6/1974 | Limpach . | |
| 3,947,686 | 3/1976 | Cooper et al. | 378/209 |
| 3,993,051 | 11/1976 | Maruyama | 5/62 X |
| 4,145,612 | 3/1979 | Cooper | 378/208 |
| 4,175,783 | 11/1979 | Pioth | 296/20 |
| 4,186,456 | 2/1980 | Huempfner | 5/430 X |
| 4,299,209 | 11/1981 | Behrens et al. | 128/87 B |
| 4,566,445 | 1/1986 | Jelsma et al. | 128/70 |

FOREIGN PATENT DOCUMENTS

| | | |
|---|---|---|
| 0102648 | 9/1983 | European Pat. Off. . |
| 2658627 | 6/1978 | Fed. Rep. of Germany . |
| 2068226 | 9/1970 | France . |
| 1077596 | 4/1966 | Sweden . |
| 1308424 | 5/1971 | United Kingdom . |

*Primary Examiner*—Michael F. Trettel
*Attorney, Agent, or Firm*—Oldham & Oldham Co.

[57] ABSTRACT

A stretcher for supporting incapacitated individuals that may be selectively positioned by two pairs of hydraulic cylinders located near each end thereof is shown. The piston rods associated with each such pair, located together with their respective cylinders on opposite sides of the stretcher, are mechanically interconnected for stability, while the cylinders associated with such pairs are hydraulically interconnected so that the cylinders can operate in tandem. The cylinder pairs each have their own pumps, operated simultaneously by a foot lever, as well as remotely controlled valving, enabling the pairs to be operated together, or independently of each other. Included pressure relief valving avoids equipment-damaging, excessive hydraulic pressures, and certain adjustable components of the stretcher are provided with spring-loaded tapered lock assemblies which allow the components to be secured in selected positions. X-ray tops are also taught which can be used in conjunction with the stretcher for X-ray examination.

18 Claims, 6 Drawing Sheets

HYDRAULIC STRETCHER DEVICE

This application is a continuation-in-part application of application Ser. No. 031,652, filed March 3, 1987 now abandoned. The invention relates to a trauma stretcher or cot for disabled, injured, or sick individuals. More particularly, this invention relates to stretchers for disabled individuals which can be desirably adjusted to facilitate their handling and treatment. Specifically this invention relates to a hydraulic stretcher device which can be positioned by means of hydraulic cylinders, and which also includes improved means for securing certain of the stretcher's adjustable features in desired positions, as well as a patient-supporting top suitable for X-ray examinations.

BACKGROUND ART

Many of the patients in hospitals and other treatment centers are inambulatory and require movable cots or stretchers for their movement in and about the centers, and to and from diagnostic or other treatment areas. It is necessary that stretchers employed for this purpose be capable of being raised or lowered, horizontally and otherwise, for ease of access by medical personnel, or for other reasons. In many cases, the patient is physically unable to move, either because of unconsciousness or infirmity; consequently, the stretcher must be extremely stable to avoid the possibility of tipping or other misadventure during patient transportation or treatment. The stretcher is often subjected to unbalanced loads during use, increasing the risk of lateral tilting, therefore, adding to the importance of structural stability. In addition, certain medical procedures require that one end of the patient be raised or lowered relative to the other end. Such adjustment, known as the Trendelenberg position, is employed, for example, in the case of cardiac arrest, where the head of the patient is lowered to allow concentration of blood in the patient's head. It is also very desirable that certain features of stretcher devices such as restraining, or safety rails, intravenous support poles, etc., be securable in several positions. In addition, in order for such features to be practical, they must be capable of being easily and reliably secured in the particular position selected.

In the past, many different types of stretchers have been devised, both of the mechanical variety, as well as some hydraulically operated devices. As might be expected, stretchers of the mechanical type are not as convenient as hydraulic stretchers, since they require hand manipulation of the apparatus associated therewith to raise, lower, and otherwise position the stretcher devices. On the other hand, hydraulic stretchers heretofore proposed have generally been unstably supported by the hydraulic cylinders employed. In addition, their hydraulic controls have not been conveniently located, and oftentimes they have been of a type difficult to operate. Furthermore, when a hydraulic stretcher is being raised, it occasionally encounters an obstructing obstacle. In previous hydraulic stretchers, operating pressures within their hydraulic systems normally continue to rise in such cases until component breakage results, due to the fact that the obstruction is unobserved, and because the mechanical advantage of the pressure inducing mechanism prevents the lack of stretcher movement from being noticed until component breaking pressures have been reached. Other disadvantages of the prior art devices include the fact that where multiple positionable features such as restraining rails, I.V. poles and the like are associated with the stretcher, the devices used to lock such features into their desired positions are relatively difficult to operate, subject to wear, and otherwise less than satisfactory. Also, when the X-ray of patients transported on stretchers is required, it necessitates transfer of the patient to a specially constructed X-ray table, an operation involving the possibility of patient injury.

DISCLOSURE OF THE INVENTION

In light of the foregoing, it is a first aspect of this invention to provide a stable, hydraulically adjustable trauma stretcher or cot for supporting disabled individuals;

it is a second aspect of the invention to furnish a hydraulic stretcher device, either end of which may be raised or lowered independently of the other end, in a Trendelenberg position;

it is a further aspect of the herein described invention to teach a hydraulic stretcher device, the hydraulic system of which includes a feature to protect the hydraulic system against destructively high pressures;

yet another aspect of this invention is to provide a hydraulic stretcher with easily accessible, simply operated hydraulic controls, designed to position the stretcher in its desired orientation;

an additional aspect of the invention is to allow a stretcher device to be fitted with adjustable features which are capable of being secured in their selected position by reliable, long wearing, and easy-to-operate adjustment locks;

another aspect of the invention described is to furnish a hydraulic stretcher device which is suitable for taking X-rays of patients supported thereon;

the foregoing and other aspects of the invention are provided by a hydraulic stretcher device comprising:

a rectangular top support assembly;

a rectangular bottom frame assembly;

two, independently operable, pairs of hydraulic positioning cylinders, and position stabilizing bars, said positioning cylinders adjustably connecting said bottom frame and top support assemblies, and said piston stabilizing bars connecting the piston rods of paired cylinders together, wherein one pair of said cylinders is located adjacent the head end of the stretcher, one cylinder on each side thereof, while another pair of said cylinders is located adjacent the foot end of the stretcher, one cylinder on each side thereof, the cylinders in each said pair being hydraulically interconnected and operating in tandem with each other;

other aspects of the invention are provided by a hydraulic stretcher device comprising:

a rectangular top support assembly;

a wheel mounted, rectangular bottom frame assembly;

two, independently operable pairs of hydraulic positioning cylinders having floating piston rods associated therewith, and piston stabilizing bars, said positioning cylinders adjustably connecting said bottom frame and top support assemblies, and said piston stabilizing bars connecting the piston rods of paired cylinders together, wherein one pair of said cylinders is located adjacent to the head of the stretcher, one cylinder on each side thereof, the cylinders in each said pair being hydraulically interconnected and operated in tandem with each other, and wherein each pair of said paired cylinders is connected to a separate pump-powered hydraulic system that includes a two-way valve that can be operated to direct hydraulic fluid to said pair, or to release said fluid therefrom, said system also including a pressure relief valve that prevents the pressure of said fluid within said system from exceeding a predetermined amount, the pumps powering the two systems being powered by a single foot pumping lever, and wherein further, said two-way valves can be operated by controls mounted on said stretcher remote from said valves;

still other aspects of the invention are provided by an X-ray permeable patient support structure comprising a laminated sheet that includes as components thereof an inner core, and covering outer surface skin adhered to the horizontal surfaces and longitudinal side edges of said core, wherein said core is formed by a material selected from the group consisting of a foamed plastic material, and balsawood, and wherein a first skin covering one of said horizontal surfaces is selected from the group consisting of a mat layer comprising carbon graphite filamentary material encapsulated in a plastic resin, and a matrix of filamentary high molecular weight polyethylene encapsulated in a plastic resin, and a second skin covering the other of said horizontal surfaces comprises a layer of fiberglass.

BEST MODE FOR CARRYING OUT THE INVENTION

Figure 1:
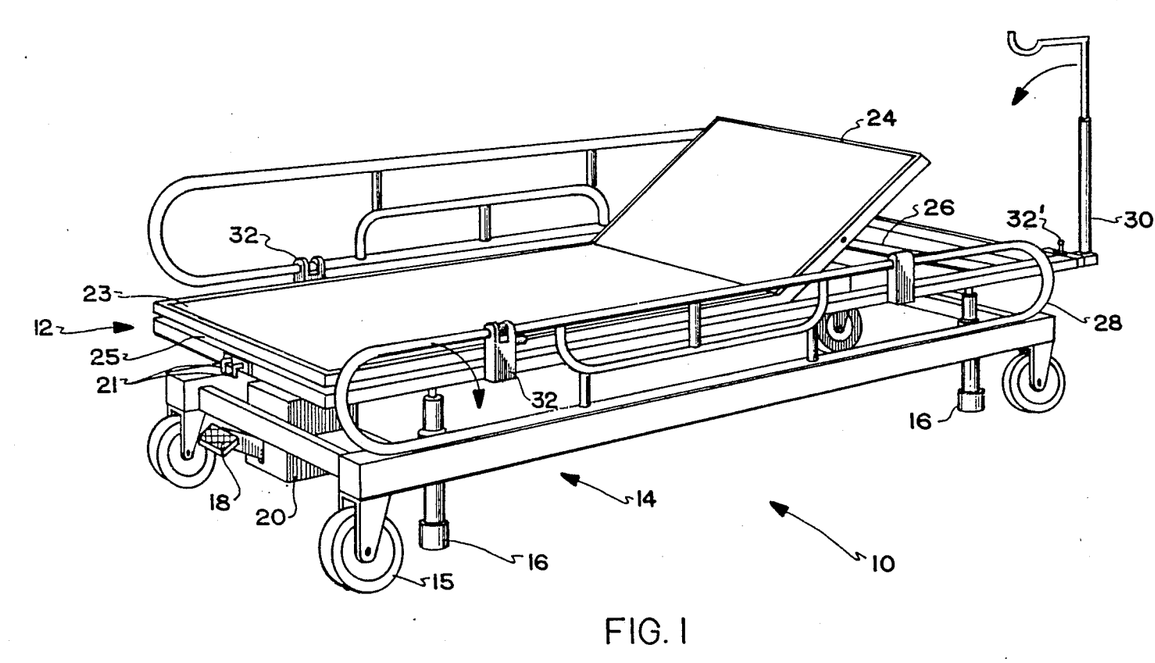
FIG. 1 is an isometric view of a hydraulic stretcher device of the invention.

FIG. 1 shows an isometric view of the hydraulic stretcher device, generally 10, of the invention comprising a top support assembly, generally 12, which is connected to a bottom frame assembly, generally 14, by means of hydraulic cylinders 16 located near each corner of the stretcher, the two cylinders at each end of the stretcher being interconnected and operated together as a pair. The hydraulic cylinders are powered by pumps operated by pump lever 18, the pumps, together with associated valving and the like being, for example, located in hydraulic system housing 20. The stretcher 10, which is mounted on caster wheels 15, is provided with a stretcher top 23 which includes a hinged back rest 24, fastened to back rest support yoke 26. The support yoke 26 is adapted to fit into notches provided in top support assembly 12, not shown, so that the angle of the back rest 24 can be adjusted to whatever angle is desired by placing the support yoke in the appropriate notch.

Stretcher 10 is also equipped with pivotal restraining rails 28 which pivot in tapered assemblies 32. Also attached to stretcher 10 is a folding, telescoping intravenous support pole 30. Both the intravenous pole 30, and restraining rails 28, are adjustable in the direction of the arrows shown adjacent such components. Also to be seen in FIG. 1 are hydraulic controls 21, the position of which determines which pair of the cylinders 16 is to be activated by the hydraulic pumps. X-ray film support access 25 illustrates the area in which X-ray film can be positioned when a patient on the stretcher is to be subjected to X-ray examination.

While various materials may be used for constructing the stretcher, such as steel, magnesium, or aluminum, the use of a hard, anodized aluminum frame is not only easy to clean, but avoids the possibility of rust or corrosion under normal circumstances. Dimensions of the stretcher may vary within a fairly broad range and still be maneuverable in a treatment center; however, a stretcher having a length of about 75 to 85 inches, and a width of about 26 to 32 inches is suitable for most purposes. The adjustable height of the stretcher may also be selected to accommodate the particular use to which the stretcher is to be put. Commonly, however, the stretcher will be designed to have an adjustable height, variable between about 20 inches to 40 inches.

Optionally, the hydraulic stretcher device of the invention may be fitted with various other features such as electrically conductive caster wheels, four wheel brake locks operable at either end of the stretcher for convenience of hospital personnel, an open storage tray associated with the bottom frame assembly 14 for personal effects of the patient, an equipment tray mounted above stretcher top 23 at the foot of the stretcher, a foot board which includes a patient chart holder mounted on the foot end of the stretcher, push bars at both the head and foot ends of the stretcher for ease in moving the stretcher, and similar conveniences.

Figure 2:
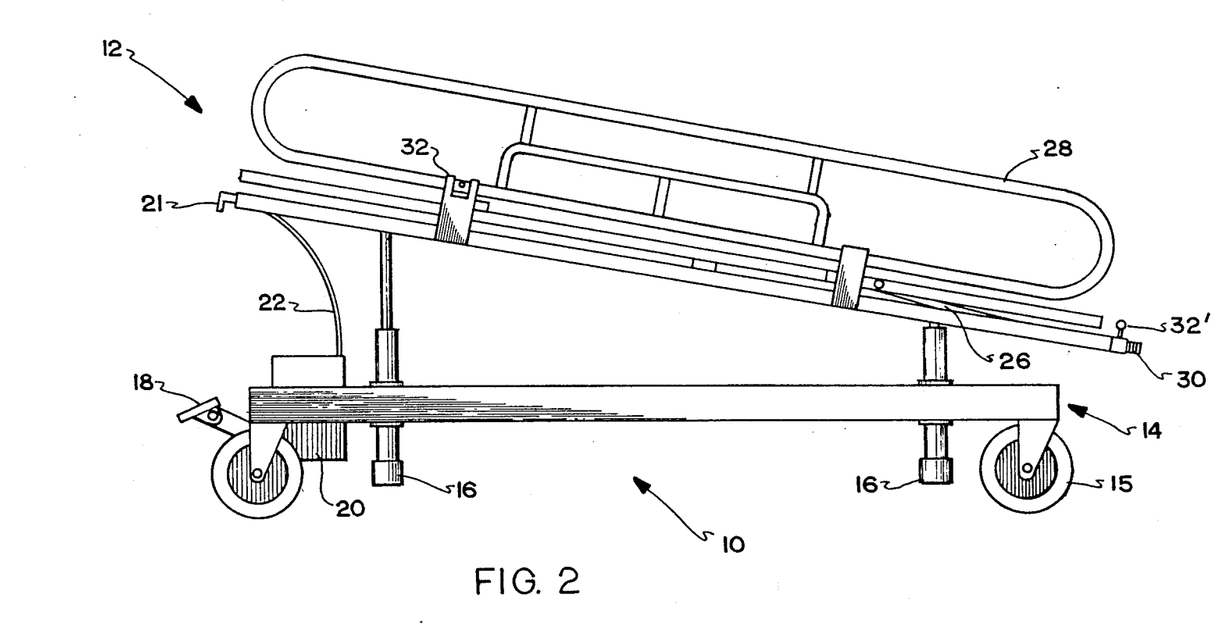
FIG. 2 is a side elevation of the stretcher device disposed in a Trendelenberg position.

FIG. 2 illustrates a side elevation of the stretcher device 10, disposed in a Trendelenberg position. In the Figure, which shows bottom frame assembly 14 connected by hydraulic cylinders 16 to top support assembly 12, pressure has been generated in the hydraulic systems by means of pump lever 18. However, hydraulic controls 21, connected to hydraulic valving by means control cable 22 have been set to provide pressurized hydraulic fluid to only one pair of hydraulic cylinders 16, in the Figure, the cylinders adjacent to hydraulic system housing 20, on each side of the stretcher. As a result, the top support assembly 12 of stretcher 10 is disposed at an angle relative to the horizontal, termed a "Trendelenberg" position. The Figure shows restraining rails 28 in their raised, or safety position, secured therein by tapered lock assemblies 32. The backrest support yoke 26 has been disengaged from the backrest adjustment notches, so that the backrest is in its lowered, inoperative mode. In addition, intravenous support pole 30 has been folded down to its storage position, in which it is secured by adjacent tapered lock assembly 32'.

The Figure illustrates a Trendelenberg position in which the foot end of the stretcher 10 has been elevated. Hydraulic controls 21 can be set, however, so that hydraulic pressure is furnished only to the pair of hydraulic cylinders 16 located at the head end of the stretcher, in the Figure, the end at which the intravenous support pole 30 is located, resulting in the head of the patient being elevated, while the patient's feet are lowered.

When the hydraulic controls 21 are set so that hydraulic pressure is furnished to each pair of hydraulic cylinders 16, i.e., at both the head and foot of the stretcher, the stretcher can be elevated in a horizontal position. By suitable use of the controls, it is possible to adjust the hydraulic pressure in each pair of cylinders so as to tilt the top of the stretcher at whatever angle is required, and/or to lower or elevate the stretcher to whatever height is required. While the hydraulic controls 21 are shown in FIG. 2 at the foot end of the stretcher, they can, optionally, be located elsewhere if desired.

Figure 3:
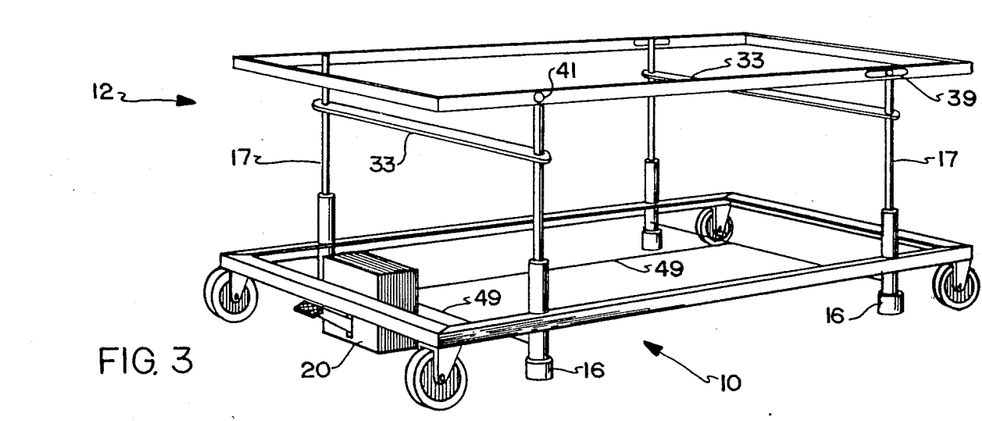
FIG. 3 is an isometric view of a simplified frame structure of the stretcher showing some of the conceptual details of the hydraulic and mechanical linkages.

FIG. 3 shows an isometric view of the framework of a stretcher 10, simplified for purposes of illustration, and detailing some its hydraulic and mechanical linkages.

The Figure shows one pair of hydraulic cylinders 16 attached to the top support assembly by means of piston rods 17, attached at pivot points 41, while another pair of hydraulic cylinders is attached by piston rods in piston rod slots 39. As top support assembly 12, is adjusted in the Trendelenberg position, the piston rods 17 attached to piston rod slots 39 are free to move in the slots, thus accommodating the required change in length of that part of the top support assembly positioned between the pairs of hydraulic cylinders 16, said change in length being necessary to accomodate the angle of the top support assembly imposed by its positioning in the Trendelenberg configuration. In FIG. 3, piston rod slot 39 is shown disposed at the right end of the stretcher, while piston rod pivot point 41 is located at the other end, adjacent to the hydraulic system housing. If desired, however, the positions of the piston rod pivot point 41 and the piston rod slot 39 can be reversed, it simply being necessary to provide a method of piston rod 17 attachment to accommodate the required increased length of the top support assembly 12 positioned between the pairs of hydraulic cylinders 16, as previously explained. The hydraulic fluid lines 49 show the interconnection between pairs of hydraulic cylinders 16, and exemplify how hydraulic fluid may be diverted to each pair of cylinders separately, from the hydraulic pump located in hydraulic system housing 20, thus allowing hydraulic fluid to be directed to the two pairs of cylinders, separately. While the interconnection of each pair of cylinders allows the end of the stretcher supported by the pair of cylinders to be raised or lowered by the cylinders operating simultaneously, it is necessary to connect the piston rods 17 of each pair with a stabilizer bar 33. The stabilizer bar 33, which is permanently attached to piston rods 17 which it connects, is necessary to prevent lateral tilting of the top support assembly 12 in those instances in which an unbalanced force is applied to one side of the table. Were it not for stabilizer bar 33, the innerconnection between the cylinders would cause hydraulic fluid to be forced from the cylinder over which the unbalanced force is applied, resulting in lowering of the side of the stretcher to which the force is applied, and producing a corresponding elevation of the opposite side, due to the displaced hydraulic fluid being forced into the opposite cylinder. The result would be an undesirable lateral tilting of the table.

Figure 4:
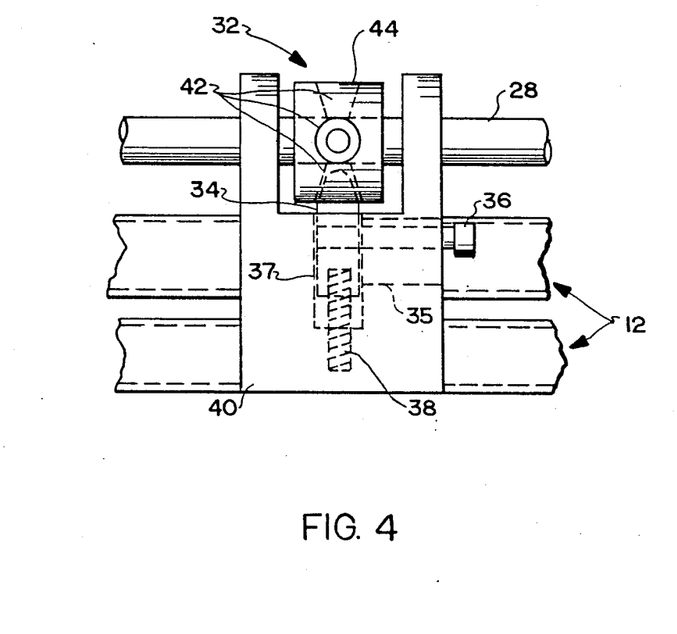
FIG. 4 is a front elevation view of a tapered lock assembly of the type used to secure adjustable features of the stretcher in selected positions.

FIG. 4 is a front elevation of a tapered lock assembly, generally 32, illustrating the mechanism employed to secure side rails 28 and intravenous support pole 30 in a selected position. In the Figure, which illustrates locking of a restraining rail 28, a bolt housing 40 is shown supported by members forming part of top support assembly 12. Contained in bolt housing 40 are locking bolt 34, which is urged by spring 38 into a locking hole 42 in the receiver 44 fixed to restraining rail 28. The lock assembly 32 is operated by applying a manual force to bolt handle 36, which is attached to locking bolt 34, in a direction which opposes the force exerted by spring 38. This causes bolt 34 to slide downward in passageway 37, disengaging the conical top of the locking bolt from a locking hole 42. The restraining rail 28 can thereupon be rotated to its desired position, a position in which a locking hole 42 is in alignment with locking bolt 34. When restraining rail 28 is in such an aligned position, and no force is applied to bolt handle 36, spring 38 will urge locking bolt 34 into the aligned locking hole 42, thus firmly securing and locking the restraining rail in position, due to the action of the spring. The tapered lock assembly 32 is not only easy to operate, but the conical, or tapered end of locking bolt 34 is rugged, long-wearing, and tends to be self-aligning. While three locking holes 42 are shown in the Figure, more or fewer such holes may be provided, depending upon the positions in which it is desired to secure the feature to be locked.

Figure 5:
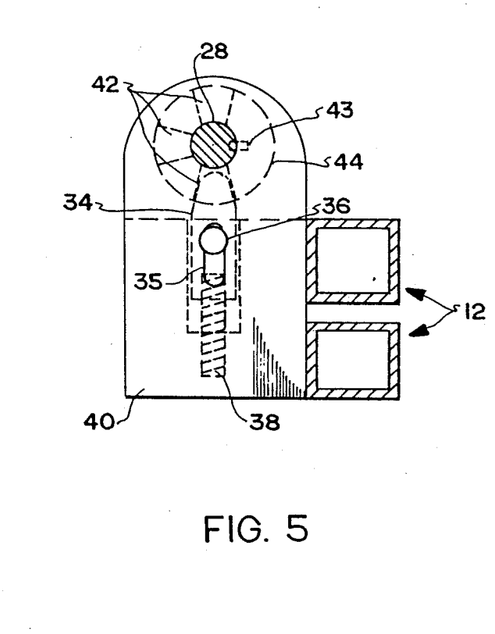
FIG. 5 is a right side elevation of the spring-loaded tapered lock assembly of FIG. 4.

FIG. 5 illustrates a right side elevation of the spring-loaded tapered lock assembly 32 of FIG. 4. Included in bolt housing 40 may be seen clarifying details of locking bolt 34, bolt handle 36, and spring 38. Also shown is adjustment slot 35 down which bolt handle 36 is forced, when adjusting restraining rail 28. The Figure shows the fastening of receiver 44 to restraining rail 28, by means of a key 43. The positioning of bolt housing 40 adjacent members of top support assembly 12 is also shown.

Figure 6:
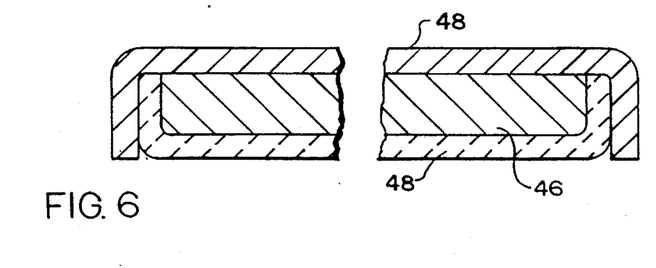
FIG. 6 shows a partial section of the lamination comprising the X-ray stretcher top.

FIG. 6 is a partial cross-section of an X-ray top which may be employed in fabricating stretcher top 23. The Figure shows a lamination comprising an inner core 46 sandwiched between two outer surface skins 48 in a "box" configuration, the surface skins being overlapped on the side edges.

In the course of conducting X-ray examinations of patients, the patient is normally supported on a table between a source of X-radiation, and the film on which an X-ray picture will be received. The material from which the table is made must possess several characteristics. First of all, it must be strong enough to support the patient, and at the same time it must be permeable to X-rays, or X-ray blockage will result in so much data loss that it will be impossible to produce a meaningful image on the film. The material must also exhibit minimal "scatter", or diffraction of X-rays passing through it, to obtain good resolution, and a sharp image. It has been found, for example, that when more than about 14% data loss is experienced, the X-ray pictures obtained are frequently too cloudy to be useful for diagnostic purposes. As used herein, the term "data loss" is defined as the amount of gamma rays produced by a radioactive isotope source which are diffracted from a straight line path by a material interposed between the source and a detector, such as a scintillation camera detector. In the past, materials containing carbon graphite mats have been employed because of their excellent X-ray permeability characteristics, rigidity, and high strength. Such, mats are produced from carbon graphite filamentary material, particularly fibers woven into fabric, surrounded by an encapsulating plastic resin so to form a substantially rigid sheet. Unfortunately, however, the material is expensive, particularly when used in a thickness sufficient to support the patient. Fiberglass, onthe other hand, while being much less expensive, has the disadvantage of producing objectionable scatter to X-rays passing through it, making sharp images difficult or impossible to obtain when the fiberglass is used in thicknesses suitable for supporting patients undergoing the X-ray diagnosis. It has now been discovered, however, that when the laminate structure described in connection with the Figure is fabricated so that the periphery of the inner core 46 transverse to the longitudinal axis of the stretcher 10 is completely covered with adherent surface skin, the equivalent of a "box" structural member is achieved, i.e., a type of structural member which exhibits great strength. The significance of forming such laminate in a box configuration in which the outer skins of the lamination are folded over each other at the edges of the X-ray top, or are otherwise configured in the course of the top's construction so that the core is entirely surrounded by the outer skins, is that the amount of carbon graphite needed to obtain sufficient strength in the stretcher top can be significantly and advantageously reduced. Furthermore, due to the great strength of the surface skin/core box type construction, not only can the thickness of the carbon graphite surface be reduced, but the significantly less expensive fiberglass can be used for one surface skin, since it can be made thin enough to reduce X-ray scatter and data loss to an acceptable point, that is below about 14%. In other words, the combination of a box-type, laminate structure, in combination with two outer surface skins, only one of which is of the carbon graphite type, the other being of fiberglass, a material previously believed to be unacceptable for X-ray purposes, provides a high strength, relatively low cost laminate, ideally suited for an X-ray diagnostic patient support surface. In addition, it has been found that such a surface is ideally suited for use in stretcher devices for reasons including its rigidity, high strength, lightweight, and relatively low cost.

Referring again to the Figure, one outer surface skin 48 will be made from a mat of carbon graphite filamentary material encapsulated in a plastic resin, typically the mat itself comprising about ⅓ of the weight of the surface skin, the balance being other components, including particularly the encapsulating plastic resin. The other surface skin 48 is comprised of fiberglass containing from about 20% to 35% by weight of fiberglass filamentary material, for example, chopped strand fiberglass, the balance being resin, such as for example, Koppers 6604-T resin. Frequently, the outer surface skins include a layer of gel coat for cosmetic reasons. It is necessary that the fiberglass surface skin thickness be in the range of about 0.01 to 0.12 inches if an undesirable level of data loss and scatter is to be avoided, and a skin thickness of about 0.01 to 0.08 provides particularly good X-ray results. Although the carbon graphite surface skin layer is more transparent to the passage of X-rays, the surface skin 28 made from it will have a similar thickness for a number of reasons including cost, structural considerations, and the like. Inner core 46 may be made from a variety of materials, however, the use of closed-cell rigid foams is especially useful. It has been found, however, that when foams with cells having a diameter greater than about 8 to 10 mils are employed, the cells themselves have a tendency to form objectionable patterns in the resulting X-ray pictures; consequently, foams with cells no greater than the size are strongly preferred. Of these, foams made from PVC or polymethylacrylimide have been found to be particularly advantageous, with the polymethylacrylimide foam being especially preferred for a variety of reasons including particularly, its lightweight and great strength. While inner cores made from foams of the type described provide a number of advantages, including ease of fabrication, balsawood cores may also be employed. Inner core 46 will usually have a thickness of from about 0.18 to 2 inches, however, in a preferred embodiment, an inner core of from about 0.12 to 2.00 inches thick is used. The components of the lamination, i.e., the outer surface skins 48 and inner core 46 are laid up in any of the ways well known in the art, and can be secured together by the adhesion obtained from a coating of resin, for example, the resin used to form the fiberglass or carbon graphite surface skins. Laminations of the type described have been found to be capable of passing up to about 94% of the X-rays directed through them, while producing negligible scatter, well below the 14% level previously referred to. Although either of the outer surface skins 48 may be in contact with the patient, that is, constitute the upper horizontal surface skin, ordinarily, the upper surface skin will be that containing the carbon graphite mat.

In a further embodiment, it has been found that a surface skin comprising a matrix of fibers, preferably in the form of a woven mat, formed from high molecular weight polyethylene, generally from about 1 to 5 million, and possessing a very high degree of crystalline orientation, for example, from about 95% to 99%, encapsulated in a plastic resin, for instance a polyester resin, may be substituted for the fiberglass skin, or for both it and the carbon graphite skin.

Such fibers, produced by a process called "gel-spinning" in which the polyethylene polymer is dissolved for the purpose of disentangling the polymer chains, and then spun, include those produced by the Allied Signal Company of Petersburg, Virginia, marketed under the Trademark "SPECTRA" fibers. The thickness of the resin encapsulated polyethylene fiber surface skins substituted for the fiberglass surface skins previously referred to, or for both those and the carbon graphite surface skins, will normally have a thickness within the same range described in connection with the substituted, surface skins. When so substituted, the encapsulated polyethylene fiber surface skins make possible construction of box-type laminated structures of the type described, which have great physical strength, as well as the ability to pass up to about 96% to 97% of the X-rays directed through such structures, and with only negligible scatter.

Figure 7:
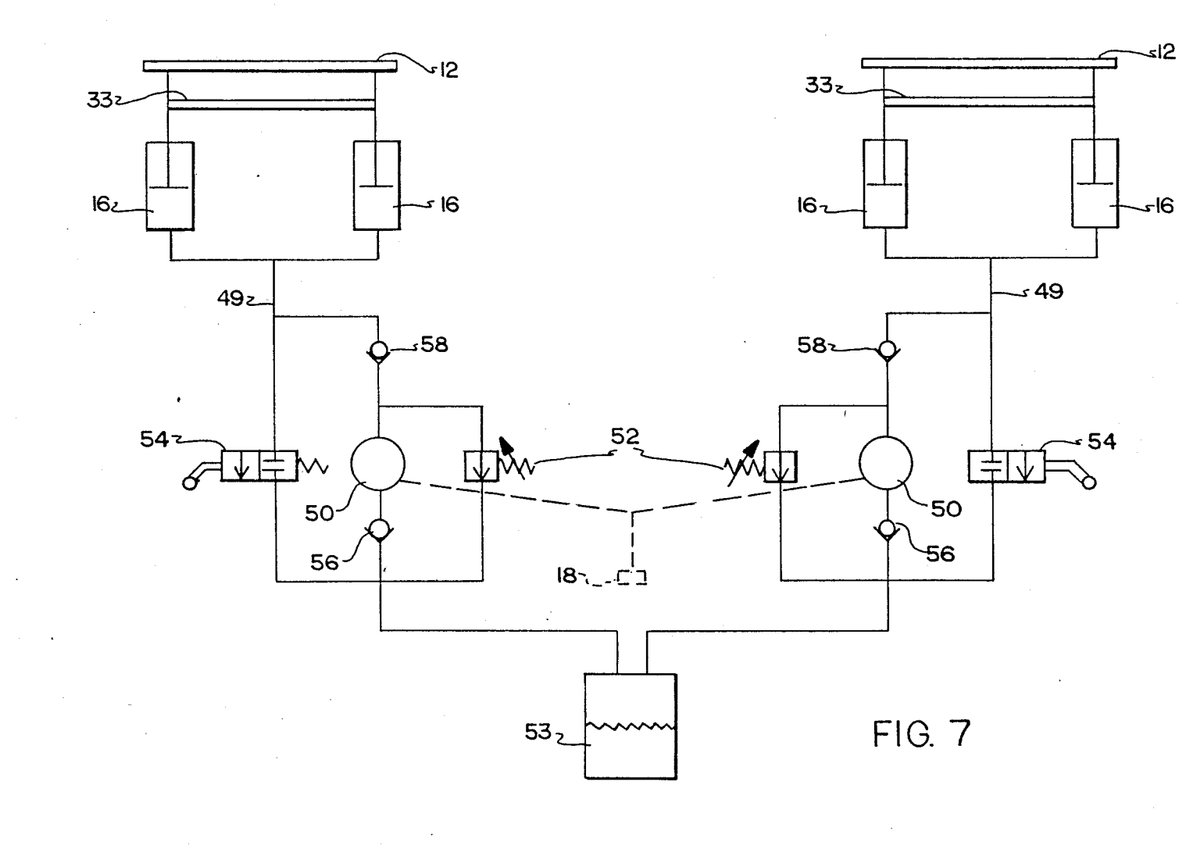
FIG. 7 is a schematic diagram of the hydraulic system of the invention.

FIG. 7 is a schematic diagram of the hydraulic system of the stretcher device. FIG. 7 shows top support assembly 12 attached to the piston rods of hydraulic cylinders 16, the piston rods of each pair of hydraulic cylinders being connected by stabilizer bars 33. The hydraulic cylinders 16 are connected by the hydraulic lines 49 to hydraulic pumps 50, which are operated by pump lever 18. Pump lever 18 is normally actuated by the foot of the user, although a hand operated lever could also be employed. If desired, separate activating pump levers 18 could be supplied for each of the pumps 50, or the pumps could be activated electrically, for example, with electricity supplied by a battery. Also shown are the hydraulic fluid reservoir 53, check valves 56 and 58, 2-way valves 54, and pressure relief valves 52. Operation of the system begins by activating the pumps 50 with pump lever 18. This draws hydraulic fluid from hydraulic fluid reservoir 53 past check valves 56 which allow the fluid to pass through them to the pumps, but prevent flow in the reverse direction. The pump forces the hydraulic fluid through check valves 58, the latter preventing reverse flow, and on to hydraulic cylinders 16 causing the piston rods, and therefore the top support assembly 12 of the stretcher device to rise. The operation described is that which occurs when two-way valves 54 are positioned in their closed, fluid blocking mode, illustrated. When the two-way valves are positioned in their open mode, hydraulic fluid is allowed to escape from hydraulic cylinders 16 and return through the two-way valves in the direction of the arrows to the hydraulic fluid reservoir 53, resulting in a lowering of the piston rods. As will be appreciated, it is possible to have one of the two-way valves 54 open, while the other remains closed, a setting which results in only one end of the stretcher device rising, positioning the stretcher device in the Trendelenberg configuration. Also, when the piston rods are in an extended position, a two-way valve 54 may be opened, releasing hydraulic therefrom, until the top support assembly 12 of the stretcher device drops to a desired lower position, at which point the two-way valve is again closed, maintaining the top support of the stretcher in the desired position. Pressure relief valves 52 are adjusted to open at a pressure just below that at which hydraulic system component damage would occur. When such pressure is reached, the pressure relief valve 52 opens, causing hydraulic fluid to recycle from the pumps 50 back to the hydraulic fluid reservoir 53.

Figure 8:
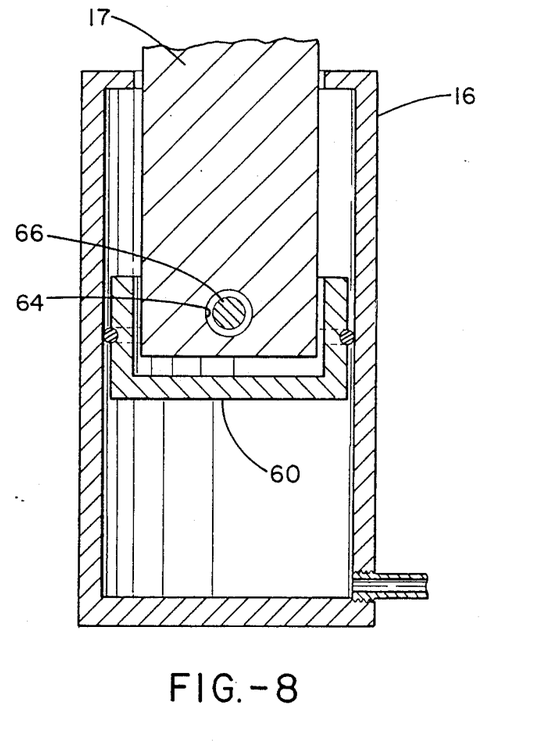
FIG. 8 shows a cross section of a free-floating hydraulic cylinder employed with the stretcher device of the invention.

FIG. 8 is a cross section of a hydraulic cylinder 16 employed with the stretcher device of the invention, illustrating the "free-floating" relationship between the piston rod 17 and the hydraulic cylinder 16.

As explained in connection with FIG. 3, it is necessary to connect the piston rod 17 of each pair of hydraulic cylinders 16 with a stabilizer bar 33 in order to prevent lateral tilting of the top support assembly 12 when unbalanced forces are applied to only one side of the table. When pairs of the hydraulic cylinders are thus inflexibly interconnected, the pistons 60 frequently have a tendency to become stuck within the cylinder, due to misalignment related to the tolerances involved in the manufacturing process. This tendency is overcome in the hydraulic stretcher device of the invention through provision of a "free-floating" cylinder-piston rod relationship. As shown in the Figure, the piston rod 17 is fastened to the piston by means of a wrist pin 66, anchored in the walls of the piston, which passes through a wrist pin bore hole 64 in the piston rod 17. The diameter of wrist pin 66 is sufficiently smaller than the wrist pin bore hole 64 through which it extends to allow the piston rod a relatively high degree of freedom to move or "float" about the wrist pin. This freedom allows the piston rod to accommodate itself to the slight misalignments which result from applied loads, manufacturing tolerances, or otherwise, avoiding binding between the piston and the cylinder wall of the type which would render the cylinder inoperable. The required difference in diameter between the wrist pin and the wrist pin bore hole will depend upon the relative dimensions of the piston rod and piston; however, in the case of a piston about 1 inch in diameter, fixed to a piston rod having a diameter of about ¾ inch, the difference in the diameter of the wrist pin and the wrist pin bore hole will commonly be about 1/16 inch. In other words, in the case of a wrist pin approximately ⅛ inch in diameter, a typical size, the wrist pin bore hole will have a diameter of about 3/16 inch.

While the Figures illustrated and the description provided, are in some instances directed to configurations of a hydraulic stretcher device having particular structural features, it will be understood that certain of the structural and configurational details may be varied within the skills available in the art without departing from the spirit of the invention.

Therefore, while in accordance with the Patent Statutes, a preferred embodiment and best mode has been presented, the scope of the invention is not limited thereto, but rather is measured by the scope of the attached claims.

What is claimed is:

1. A hydraulic stretcher device comprising:
   a rectangular top support assembly;
   a bottom frame assembly;
   two independently operable, pairs of hydraulic positioning cylinders, said positioning cylinders adjustably connecting said bottom frame assembly and said top support assembly;
   wherein one pair of said cylinders is located adjacent to the head end of the stretcher, one cylinder on each side thereof, while another pair of said cylinders is located adjacent the foot end of the stretcher, one cylinder on each side thereof, each of said cylinders having a free-floating piston and a piston rod associated therewith, each of said piston rods being operatively connected to said top support assembly;
   separate pump powered hydraulic systems for each of said pairs of cylinders, one pair of said cylinders being connected to one of said hydraulic systems and the other hydraulic system being connected to the other pair of said cylinders, each hydraulic system including a pump, a two-way valve that can be operated to direct hydraulic fluid to said pairs, or to direct said fluid therefrom, and a pressure relief valve that prevents the pressure of said fluid within said system from exceeding a predetermined amount;
   the cylinders in each such pair being hydraulically connected and operating in tandem with each other;
   means for permitting horizontal movement of the upper ends of the piston rods of one pair of cylinders; and
   a pair of piston stabilizing bars, each of said piston stabilizing bars connecting the piston rods of paired cylinders together.

2. A hydraulic stretcher device according to claim 1 wherein the piston rod of each said hydraulic positioning cylinders is attached to its associated piston by means of a wrist pin connected to said piston which passes through a wrist pin bore hole in said piston rod, the difference in diameter between said wrist pin and said wrist pin bore hole being sufficient to permit said cylinders and said piston rods to accomodate misalignment.

3. A hydraulic stretcher device according to claim 1 in which, both of said pumps are operated by a single pumping lever, wherein each of the two-way valves can be remotely operated by controls mounted on said device, apart from said valves.

4. A hydraulic stretcher device according to claim 3 which includes adjustable restraining rails on both sides of said device, each of said rails being held by a spring-loaded tapered lock assembly.

5. A hydraulic stretcher device according to claim 3 which includes a folding intravenous pole which is secured in position by a spring-loaded tapered lock assembly.

6. A hydraulic stretcher device according to claim 1 in which said hydraulic systems are controlled by a single actuator.

7. A hydraulic stretcher device according to claim 1 in which said means for permitting horizontal movement of the upper ends of the piston rods comprise a pair of slots.

8. A hydraulic stretcher device comprising:
a rectangular top support assembly;
a wheel mounted, rectangular bottom frame assembly;
two, independently operating, pairs of hydraulic positioning cylinders having floating piston rods associated therewith, and
piston stabilizing bars, said positioning cylinders adjustably connecting said bottom frame and top support assemblies, and said piston stabilizing bars connecting the piston rods of paired cylinders together, wherein one pair of said cylinders is located adjacent to the head end of the stretcher, one cylinder on each side thereof, while another pair of said cylinders is located adjacent to the foot end of the stretcher, one cylinder on each side thereof, the cylinders in each such pair being hydraulically interconnected and operable in tandem with each other, and wherein each pair of said paired cylinders is connected to a separate pump-powered hydraulic system that includes a two-way valve that can be operated to direct hydraulic fluid to said pair, or to release said fluid therefrom, said system also including a pressure relief valve that prevents the pressure of said fluid within said system from exceeding a predetermined amount, the pumps powering the two systems being operated by a single foot pumping lever, and wherein further, said two-way valves can be operated by controls mounted on said stretcher remote from said valves.

9. A hydraulic stretcher device according to claim 8 wherein the piston rod of each said hydraulic positioning cylinder is attached to its associated piston by means of a wrist pin connected to said piston which passes through a wrist pin bore hole in said piston rod, the difference in diameter between said wrist pin and said wrist pin bore hole being sufficient to permit said cylinders and said piston rods to accomodate misalignment.

10. An X-ray permeable patient support structure comprising a laminated sheet that includes as components thereof an inner core having a pair of horizontal surfaces and also having longitudinal side edges, and first and second outer surface skins adhered to respective horizontal surfaces, one of said skins also being adhered to the longitudinal side edges of said core, said structure being in the form of a box structure wherein the first and second outer surface skins overlap each other on said side edges, wherein said core is formed by a material selected from the group consisting of a foamed plastic material, and balsawood, and wherein said first skin covering one of said horizontal surfaces is composed of material selected from the group consisting of a mat layer comprising carbon graphite filamentary material encapsulated in a plastic resin, and a matrix of filamentary high molecular weight polyethylene encapsulated in a plastic resin, and said second skin covering the other of said horizontal surfaces is composed of a layer of material selected from the group consisting of a layer of fiberglass in a plastic resin and filamentary high molecular weight polyethylene encapsulated in a plastic resin.

11. An X-ray permeable patient support structure according to claim 10 wherein said second skin is composed of filamentary high molecular weight polyethylene encapsulated in a plastic resin.

12. A patient support structure according to claim 10 in which said core is fabricated from a closed-cell foamed plastic material in which the cells are no more than about 8 to 10 mils in diameter.

13. A patient support structure according to claim 10 in which said foamed plastic material is comprised of polymethylacrylimide.

14. A patient support structure according to claim 10 in which no more than about 14% of gamma radiation directed through said horizontal surfaces at right angles thereto is deflected from a straight line vertical path.

15. A patient support structure according to claim 10 wherein said core is from about 0.19 inch to about 2.00 inches thick, while each of the skins covering said horizontal surfaces is from about 0.01 inch to about 0.08 inch thick.

16. A patient support structure according to claim 10 in which said second skin is composed of fiberglass in a plastic resin.

17. A hydraulic stretcher device comprising:
a rectangular top support assembly;
a bottom frame assembly;
two independently operable pairs of hydraulic positioning cylinders, said positioning cylinders adjustably connecting said bottom frame assembly and said top support assembly;
wherein one pair of said cylinders is located adjacent to the head end of the stretcher, one cylinder on each side thereof, while another pair of said cylinders is located adjacent the foot end of the stretcher, one cylinder on each side thereof, each of said cylinders having a free-floating piston and a piston rod associated therewith, each of said piston rods being operatively connected to said top support assembly; separate pump powered hydraulic systems for each of said pairs of cylinders, one pair of said cylinders being connected to one of said hydraulic systems and the other hydraulic system being connected to the other pair of said cylinders, each hydraulic system including a pump, a two-way valve that can be operated to direct hydraulic fluid to said pairs, or to direct said fluid therefrom, and a pressure relief valve that prevents the pressure of said fluid within said system from exceeding a predetermined amount;
the cylinders in each such pair being hydraulically connected and operating in tandem with each other;
a pair of piston stabilizing bars, each of said piston stabilizing bars connecting the piston rods of paired cylinders together;
said rectangular top support assembly including an X-ray permeable patient support structure fabricated from a lamination configured in a box structure which includes a core having an upper horizontal surface and a lower horizontal surface, each of said surfaces being covered with a surface skin wherein said core layer is formed from a foamed plastic material, or from balsa wood, and wherein a first surface skin covering one horizontal surface is made of a material selected from the group consisting of a mat layer comprising carbon graphite filamentary material encapsulated in a plastic resin, and a matrix of filamentary high molecular weight polyethylene encapsulated in a plastic resin, and a second skin covering the other of said horizontal surfaces is a layer of fiberglass in a plastic resin or filamentary high molecular weight polyethylene encapsulated in a plastic resin, said core being from about 0.19 inch to 2.00 inches thick, while each of said surface skins is from about 0.01 inch to 0.08 inch thick.

18. A hydraulic stretcher device according to claim 17 wherein said second surface skin comprises a matrix of filamentary high molecular weight polyethylene encapsulated in a resin.

* * * * *